(12) United States Patent
Lee et al.

(10) Patent No.: US 9,567,578 B1
(45) Date of Patent: Feb. 14, 2017

(54) CELL LINE CONTAINING A KNOCKOUT OF THE GLUTAMINE SYNTHETASE (GS) GENE AND A METHOD OF PRODUCING TARGET PROTEINS USING A GS KNOCKOUT HEK293 CELL LINE

(71) Applicant: Korea Advanced Institute of Science and Technology, Daejeon (KR)

(72) Inventors: Gyun-Min Lee, Daejeon (KR); Da Young Yu, Daejeon (KR); Soo Min Noh, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/138,165

(22) Filed: Apr. 25, 2016

(30) Foreign Application Priority Data

Jan. 4, 2016  (KR) .................. 10-2016-0000374

(51) Int. Cl.
| | | |
|---|---|---|
| *C12N 15/63* | (2006.01) | |
| *C12N 9/00* | (2006.01) | |
| *C12N 5/071* | (2010.01) | |
| *C12N 15/85* | (2006.01) | |

(52) U.S. Cl.
CPC ............... *C12N 9/93* (2013.01); *C12N 5/0686* (2013.01); *C12N 15/85* (2013.01); *C12Y 603/01002* (2013.01)

(58) Field of Classification Search
CPC .................................................. C12N 15/163
USPC ............................................. 435/252.3, 69.1
See application file for complete search history.

(56) References Cited

U.S. PATENT DOCUMENTS 8,153,399 B2 * 4/2012 Liu .......................... C12N 9/22
435/15

OTHER PUBLICATIONS

Cho et al., (2013), "Targeted genome engineering in human cells with the Cas9 RNA-guided endonuclease," Nature Biotechnology, 31(3): 230-232 and Supplementary Information.
GenBank Accession No. NG_013347.2, Sep. 2016.
Ghaderi et al., (2012), "Production platforms for biotherapeutic glycoproteins. Occurrence, impact, and challenges of non-human sialylation," Biotechnology and Genetic Engineering Reviews, 28: 147-176.
Noh et al., (2013), "Development of recombinant Chinese hamster ovary cell lines for therapeutic protein production," Current Opinion in Chemical Engineering, 2(4):391-397 (Abstract only).

* cited by examiner

*Primary Examiner* — Maryam Monshipouri
(74) *Attorney, Agent, or Firm* — Lathrop & Gage LLP

(57) ABSTRACT

The present invention relates to a novel GS (glutamine synthetase) gene knock out transgenic HEK293 (human embryonic kidney 293) cell line and a production method of a target protein using the said transgenic HEK293 cell line. Particularly, the present inventors eliminated the expression of GS in the HEK293 cells in order to overcome a barrier of the cell line selection caused by the over-expression of GS, for producing a target protein by GS/MSX system, by which the efficiency of the cell line selection for the high production of a target protein would be increased and accordingly the protein production by the selected cell line would be increased, suggesting that the human originated transgenic HEK293 cell line could be efficiently used for the production of a target protein.

8 Claims, 8 Drawing Sheets

Control    HEK293
                   GS-KO

GS

β-actin

Figure 2C

CELL LINE CONTAINING A KNOCKOUT OF THE GLUTAMINE SYNTHETASE (GS) GENE AND A METHOD OF PRODUCING TARGET PROTEINS USING A GS KNOCKOUT HEK293 CELL LINE

CROSS-REFERENCE TO RELATED APPLICATIONS

This patent application claims the benefit of priority from Korean patent application no. KR 10-2016-0000374, filed on Jan. 4, 2016, the contents of which are incorporated herein by reference.

BACKGROUND OF THE INVENTION

1. Field of the Invention

The present invention relates to a glutamine synthetase knock out transgenic HEK293 (Human embryonic kidney 293) cell line and a production method of a target protein using the transgenic cell line.

2. Description of the Related Art

The size of the world-wide protein medicine market is as big as almost 15.7 billion dollars as of 2011. This market is expected to grow continuously to 20 billion dollars in 2016. Mammalian cells are the most widely used system in the production of biomedicine (antibody for treatment, growth factor, hormone, etc), which are exemplified by HEK293 cells, CHO (Chinese hamster ovary) cells, NS0 (mouse myeloma) cells, and PER.C6 (human retinal cells). Among them, CHO cells have been used for the production of ⅓ of the total animal cell originated protein medicine but there is some concern about the characteristics of the produced protein thereby because of the rodental characteristics of the cells.

The difference in the quality of the produced protein caused by such cell line origins is attributed to the post-translational modification (PTM). In particular, the glycosylation process during which a sugar chain is added seems to have the biggest effect on the efficacy of the protein medicine product. The component and structure of a sugar chain attached onto a protein medicine have an effect on the persistence of an applied medicine and the medicinal effect of the same. When it is administered repeatedly, it can also be a reason of immunogenicity. The structure of the sugar chain adhering on the protein in CHO cells is the closest to that of human cells, compared with other rodent originated cells. However, it still contains such sugar chain structures that human cells do not contain which are N-glycosyl-neuraminic acid (Neu5Gc) and Galα1-3Galβ1-GlcNAc-R (α-Gal), and these sugar chains might cause an immune response, leaving a question in stability (Ghaderi et al., Biotechnol. Genet. Eng. Rev. 2012, 28:147-75). Therefore, it is necessary to develop a human originated production cell line that can be a useful system for the production of a protein that is equally qualified to the protein of human.

The human originated cell lines that have been used for the production of a protein medicine are HEK293, F2N, and PER.C6, etc. Among them, HEK293 cell line has a great potential for the production of a medicinal protein as a human originated host cell. And the reasons for that potential are as follows:

(1) HEK293 cell line has been most widely used in the field of science whose cellular characteristics have been continuously studied, so that the relevant information regarding the cell line is rich. (2) HEK293 cell line can be suspending-cultured in a serum free medium, so that it can be used for the high concentration cell culture and for the mass-production in an industrial scale. (3) The protein medicine produced in HEK293 cell line has been approved by such supervisory institutions as FDA and EMA, proving the stability of HEK293 as a production cell line. However in the real industrial field, HEK293 cell line is only applied for transient transfection system for the screening of a target protein for the protein production, and there is no stable protein production system for the continuous high concentration production established so far, suggesting that HEK293 is not widely used as expected for the mass production of a target protein as a real medicinal product.

As a method for producing a protein medicine with high concentration using an animal cell line, a cell line selection technique using a gene amplification system has been developed. The most common systems are DHFR/MTX (dihydrofolate reductase/methotrexate) and GS/MSX (glutamine synthetase/methionine sulfoximine). These two systems are mainly used to produce a protein in CHO cell line. Particularly, a host cell is transfected with a plasmid comprising a therapeutic recombinant protein gene and a selection marker gene, and then a cell line is selected in an environment in the presence of an inhibitor corresponding to each enzyme gene. The transgenic cell line designed to be suitable for the production of a target protein amplified the selection marker gene included in the plasmid in order to overcome the added inhibitor, during which the therapeutic recombinant protein included together in the plasmid is also amplified. As a result, the cell line displaying a high productivity per cell ($q_p$) can be selected, with which the continuous high concentration target protein production can be achieved. The DHFR/MTX and GS/MSX systems are widely used in the industry. In particular, GS/MSX system makes the selection of a high production clone possible simply by one time MSX amplification, so that the time for the cell line construction can be decreased with this system. Therefore, it is most widely used recently. A recombinant HEK293 cell line that can produce a target protein can be prepared by transfecting the HEK293 cell line with a therapeutic recombinant protein gene by using the GS/MSX system (Noh et al., Curr. Opin. Chem. Eng. 2013, 2:391-7).

In order for the gene amplification system to be effective, it is important to inhibit the effect of the selection marker gene included in the host cell in the course of the gene amplification mediated by an inhibitor. If a selection marker gene is already expressed at a high concentration in a host cell line, the endogenous selection marker gene is amplified together with the introduced protein production plasmid in the host cell despite an inhibitor is treated during the selection, so that the efficiency of the amplification of the therapeutic recombinant protein gene is accordingly reduced and the productivity per cell ($q_p$) is arrested.

In the case of using the DHFR/MTX system, the selection marker gene dhfr knockout CHO dhfr(-) cell line has been developed. For the GS/MSX system, NS0 or CHO-K1 cell line expressing the selection marker gene gs at a low level endogenously is used.

The present inventors noticed the high resistance against MSX, the GS inhibitor, in HEK293 cell line which was resulted from the endogenously, highly expressed GS protein (see FIG. 1). Therefore, the inventors confirmed that HEK293 cell line cannot be introduced in GS/MSX system without gene manipulation unlike the previous NS0 or CHO-K1 host cells. The present inventors introduced the gene editing method CRISPR (Clustered Regularly Interspaced Short Palindromic Repeats; CRISPR/cas9, Cho et al., Nat. Biotechnol. 2013, 31(3): 230-2) targeting gs, the selection marker gene of gene amplification system in HEK293 cell line. As a result, the inventors constructed the glutamine synthetase (gs) gene knockout HEK293 cell line. Owing to the knockout of gs gene there, cell line selection can be efficiently performed by using MSX. The present inventors confirmed that the selection efficiency of a cell line for the production of a target protein was improved by increasing the concentration of MSX, leading to the completion of this invention.

SUMMARY OF THE INVENTION

It is an object of the present invention to make the selection of a clone for the high production of a target protein possible in HEK293 cell line by using GS/MSX system by eliminating the MSX (methionine sulfoximine) resistance in HEK293 (human embryonic kidney 293) cell line caused by the endogenous expression of GS (glutamine synthetase) protein.

To achieve the above object, the present invention provides a gs (glutamine synthetase) gene knockout novel transgenic HEK293 (human embryonic kidney 293) cell line.

In addition, the present invention provides a method for producing a target protein using the transgenic HEK293 cell line which is prepared by transfecting the transgenic HEK293 cell line with a vector comprising a gene encoding the target protein.

Advantageous Effect

The transgenic HEK293 (human embryonic kidney 293) cell line of the present invention loses glutamine synthesis ability because of the knockout of gs (glutamine synthetase), resulting in the elimination of MSX (methionine sulfoximine) resistance and the increase of glutamine dependency. So, in the course of the selection of a production cell line using GS/MSX system, HEK293 cell line is transfected with a vector comprising gs gene and then the gs gene included in the vector is expressed high enough to cope with the MSX concentration, leading to the efficient cell line selection. Therefore, the GS/MSX system mediated production cell line selection can be also efficiently achieved in HEK293 cell line. As a result, the said gs knockout HEK293 cell line and the production method of a target protein using the transgenic HEK293 cell line can be efficiently used to increase the productivity and the production amount of the target products such as antibody and cytokine and also to open a new market of the interest.

BRIEF DESCRIPTION OF THE DRAWINGS

The application of the preferred embodiments of the present invention is best understood with reference to the accompanying drawings, wherein:

FIG. 2C is a diagram illustrating the genotype of the gs gene exon 4 knockout HEK293 cell prepared by using CRISPR. Compared with the wild type, the deleted nucleotides are presented by colons and the added nucleotide sequences are presented by the red. Compared with the allele A and B of the wild type sequence, the allele C, D, and E of the transgenic HEK293_GS-KO are presented in the left. The prepared HEK293 GS-KO cell is the heterozygote knockout (KO) displaying the deletion pattern of different base pairs.

DETAILED DESCRIPTION OF THE INVENTION

Figure 1:
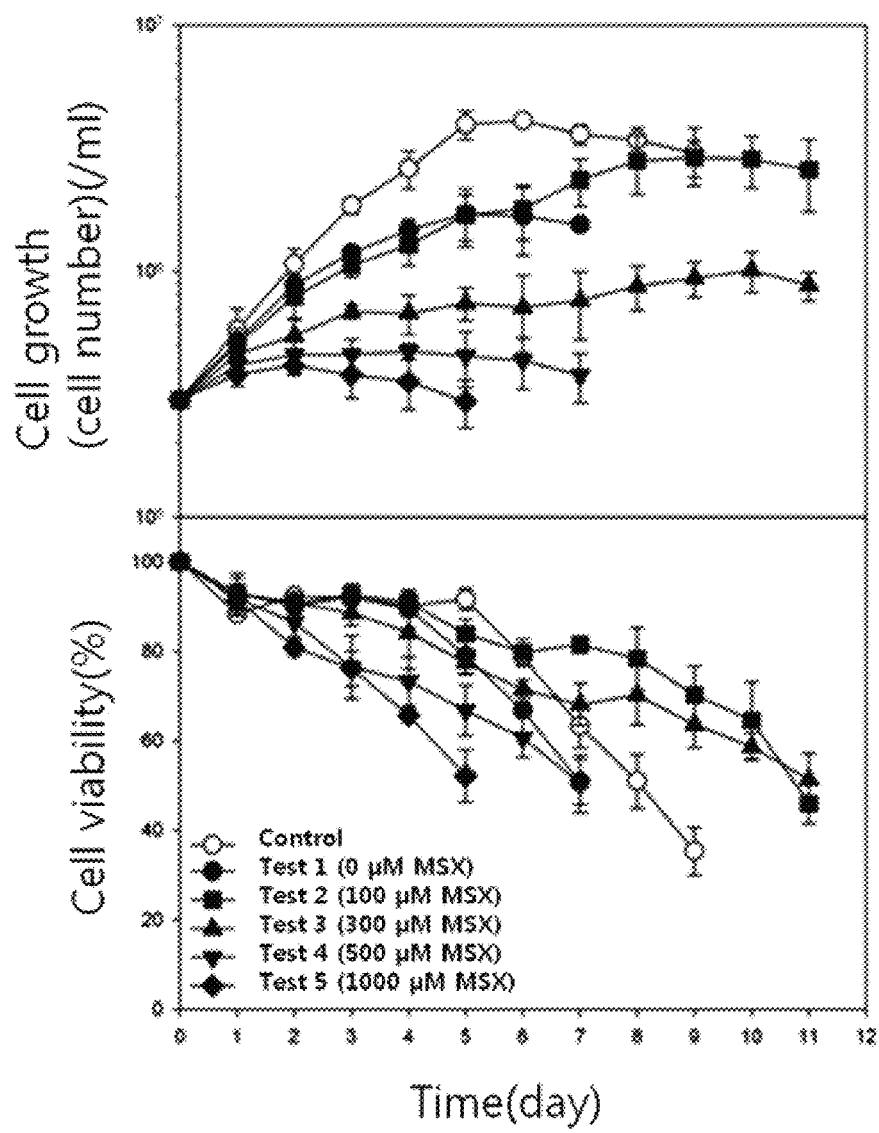
FIG. 1 is a graph illustrating the cell growth and the cell viability according to the batch culture of HEK293 (human embryonic kidney 293) cells in a 50 ml added with MSX at different concentrations.

Hereinafter, the terms used in this invention are described in more detail.

The term "batch culture" used in this invention indicates the method of culture that continues until the first supplied raw materials are all consumed without additional supply, with which the concentration of substrates, the concentration of metabolites, and the density of cells are changed continuously over the culture time.

The term "knockout", "elimination", and "deletion" in this invention can be used interchangeably. This term means any addition or loss of a target gene sequence of cell genome so that the protein expression mediated by the target gene is completely removed.

The term "clone" and "cell line" can be used interchangeably, which both indicate a cell group having the same characteristics.

In this invention, "CRISPR" is the system composed of sgRNA (guide RNA) complementarily binding to the target genome and Cas9 protein that can cut the genome gene by binding to sgRNA and the target genome simultaneously. As a result, when sgRNA vector and Cas9 vector are expressed temporarily in cells together at the same time, sgRNA and Cas9 protein are produced to change gs gene sequence, leading to the suppression of the GS protein expression.

Hereinafter, the present invention is described in detail.

The present invention provides a GS (glutamine synthetase) knockout novel transgenic HEK293 cell line.

The transgenic HEK293 cell line was deposited at Korean Collection for Type Cultures (KCTC), Korea Research Institute of Bioscience and Biotechnology (KRIBB), 181 Ipsin-gil, Jeongeup-si, Jeollabuk-do 56212, Republic of Korea, on Feb. 17, 2016 according to the Budapest Treaty for the purposes of patent procedure. The cell line has been accorded the deposit number Accession No: KCTC12978BP. Upon grant of a patent, all restrictions imposed by the depositor on the availability to the public of the deposited biological material will be irrevocably removed.

The cell line is preferably characterized by the mutation of the nucleotide sequence in the $4^{th}$ exon of gs gene. gDNA of Homo sapiens gs gene can be found in SEQ. ID. NO: 9 (see also GenBank NG_013347.2).

The nucleotide sequence that has mutation in the $4^{th}$ exon of gs gene is preferably TTTTTGCCCCAGAGTTGCCT-GAGTGGAATTT (SEQ. ID. NO: 1), and characterized by the addition of the nucleotide A to the sequence or the deletion of 11 nucleotides therefrom.

The cell line is preferably originated from human, precisely the transformed HEK293 cell line, or can be constructed with the cell lines originated from HEK293 (HEK293 EBNA, HEK293.sus, HEK293T, etc).

The cell line above is dependent on glutamine but has no resistance against MSX (methionine sulfoximine). It is thus preferred to increase the selection efficiency of the production cell line mediated by MSX by using GS as the selection marker protein.

In a preferred embodiment of the present invention, the inventors constructed GS knockout HEK293 cell line (HEK293_GS-KO) by deleting gs gene. Particularly, CRISPR (the vector expressing sgRNA targeting gs gene and the vector expressing Cas9 protein) was introduced in the wild type HEK293 host cells adhesion-cultured in DMEM supplemented with 7% (v/v) fetal bovine serum, 1×GSEM (glutamine synthetase expression medium, Sigma-Aldrich, St. Louis, Mo., USA), and glutamine. Then, the cells that could not grow in the absence of glutamine were selected. Western blotting was performed to select the cell line that did not express GS protein (see FIGS. 2A and 2B). The exon #4 of the genomic DNA gs gene of the GS knockout cell line was analyzed. The cell line wherein the change of gene sequence on the targeted area has been observed in every homologous chromosome pair was selected to construct gs gene knockout HEK293 cell line (HEK293_GS-KO) (see FIG. 2C). The prepared HEK293_GS-KO cell line was deposited at Korean Collection for Type Cultures (KCTC), Korea Research Institute of Bioscience and Biotechnology (KRIBB), 181 Ipsin-gil, Jeongeup-si, Jeollabuk-do 56212, Republic of Korea, on Feb. 17, 2016 according to the Budapest Treaty for the purposes of patent procedure. The cell line has been accorded the deposit number Accession No: KCTC12978BP. Upon grant of a patent, all restrictions imposed by the depositor on the availability to the public of the deposited biological material will be irrevocably removed.

The present inventors cultured the prepared gs gene knockout HEK293 cell line in order to investigate the glutamine dependency of the cell line. The wild type HEK293 cells and the gs gene knockout HEK293 cells were cultured in DMEM supplemented with 10% (v/v) dialyzed FBS (dFBS) and 1×GSEM. At this time, two different DMEMs, DMEM containing 4 mM glutamine and glutamine-free DMEM, were used to make the culture environment with and without glutamine. The wild type HEK293 cell line grew normally in both environments, that is in the presence and in the absence of glutamine. On the other hand, the growth of the gs knockout HEK293 cell line was inhibited in the glutamine-free medium because of the knockout of GS protein and accordingly the cell viability dropped rapidly (see FIG. 3). GS protein induces the synthesis of endogenous glutamine to maintain cell growth and survival, which is though inhibited by MSX. High GS expression in HEK293 cells inhibits the MSX selection and as a result the selection of the cell line having a high productivity is limited. However, when gs gene is knocked out, the glutamine dependency and the reactivity to MSX are increased, suggesting that the selection efficiency of HEK293 cell line in GS/MSX system can be increased.

The present inventors investigated the MSX reactivity of the gs gene knockout HEK293 cell line and the possibility to increase the selection efficiency of the high production cell line by MSX mediated by the increased glutamine dependency. Particularly, the control cells normally expressing GS protein (wild type HEK293 host cells) or the HEK293_GS-KO cells were transfected with the vector containing the selection marker gene gs and the target protein (monoclonal antibody) gene together. Then, the transformed cells were cultured in the medium not supplemented with glutamine but supplemented with MSX at the concentrations of 0 µM, 25 µM, 50 µM, and 100 µM in order to select the clone that produced the target protein. The protein productivity of the selected clone was investigated. While the clones selected from the control cell line did not produce the target protein, the clones selected from the HEK293 GS-KO produced the target protein stably. As the concentration of MSX was increased, the protein productivity of the selected clones was also increased (see FIG. 3). In conclusion, the selection efficiency of the production cell line using MSX was increased by transforming the HEK293_GS-KO cell line.

Therefore, the HEK293 GS-KO confirms the possibility of applying the selection process of the production cell line using GS/MSX system to the human originated HEK293 cell line. That is, when the cells are introduced with the vector encoding a target protein and the selection marker gene (gs) and thereafter the production cell line is selected by using MSX, the efficiency of selecting the cell line displaying a high productivity can be increased. Thus, the novel transgenic HEK293 cell line wherein gs gene is knocked out by CRISPR can be effectively used.

The present invention also provides a method for producing a target protein using the transgenic HEK293 cell line which is prepared by transfecting the transgenic HEK293 cell line with a vector comprising a gene encoding a target protein.

The method above is composed of the following steps, but not always limited thereto:

1) constructing the transformed HEK293 cell line manipulated to express a target protein by introducing a vector containing the gene encoding the target protein and gs gene together into the transgenic HEK293 cell line of the present invention;

2) culturing the cell line prepared in step 1); and 3) separating and purifying the target protein produced in the cell line of step 2).

The method for producing a target protein above can be accomplished by transfecting the transgenic HEK293 cell line with a vector containing the gene encoding the target protein.

In the method above, the GS knockout novel transgenic HEK293 cell line of step 1) is preferably the one deposited under the accession number of KCTC12978BP.

The cell line is preferably characterized by the mutation of the nucleotide sequence in the 4$^{th}$ exon of gs gene.

The nucleotide sequence that has mutation in the 4$^{th}$ exon of gs gene is preferably TTTTTGCCCCAGAGTTGCCTGAGTGGAATTT (SEQ. ID. NO: 1), and characterized by the addition of the nucleotide A to the sequence or the deletion of 11 nucleotides therefrom.

In the method above, the target protein of step 1) is exemplified by soluble TNF receptor, soluble IL-4 receptor, soluble IL-1 type II receptor, soluble CD40 ligand, CD39, CD30, CD27, TEK/ORK, IL-15 receptor, GM-CSF, RANKL, RANK, TRAIL, soluble TRAIL receptor, tissue plasminogen activator, factor VIII, factor IX, apolipoprotein E, apolipoprotein A-I, IL-2 receptor, IL-2 antagonist, alpha-1 antitrypsin, growth hormone, insulin-like growth factors, parathyroid hormone, interferon, monoclonal antibody (mAb), erythropoietin (EPO), thrombopoietin (TPO), and Fc containing fusion protein.

To investigate whether or not the gs gene knockout HEK293 cell line prepared above could be used for the production of a target protein, the present inventors cultured the transgenic HEK293 cell line in 4 mM glutamine DMEM supplemented with 7% (v/v) FBS and 1×GSEM. The cell line was transfected with a vector containing the target protein gene and gs gene together. Then, the cell line introduced with the vector containing the target gene was selected in the glutamine-free DMEM supplemented with 10% (v/v) dFBS, 1×GSEM, and MSX at the concentrations of 0 µM, 25 µM, and 50 µM. At this time, the cell line confirmed to be able to grow in the glutamine-free medium and to show the MSX resistance was selected as a pool or as each clone. In a preferred embodiment of the present invention, the clones that could produce a target protein were selected. Total 50 clones were selected according to the different concentrations of MSX and the production of the target protein was compared. The control group prepared by introducing the gene encoding the monoclonal antibody into the wild type HEK293 host cell line (HEK293 control), and the 50 clones prepared by introducing the gene encoding each monoclonal antibody protein into the gs gene knockout HEK293 host cells (HEK293_GS-KO) were adhesion-cultured in the selection medium. On the 6$^{th}$ day of culture, the concentration of the monoclonal antibody was quantified. As a result, the target protein production in the protein production clones prepared from the HEK293_GS-KO was increased MSX dose-dependently. However, the clones prepared from the HEK293 control did not produce the target protein regardless of the concentration of MSX used for the selection (see FIG. 4).

Figure 5A:
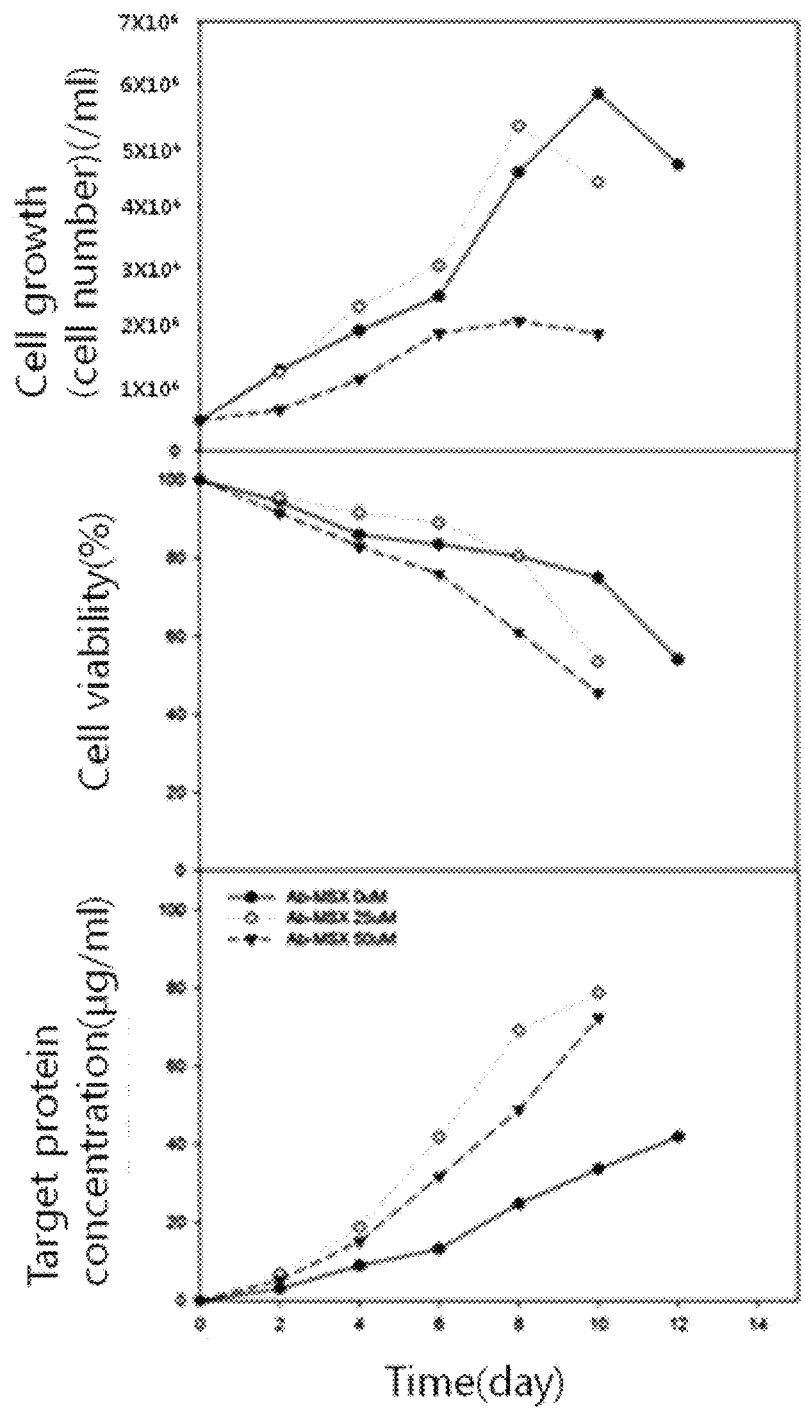
FIG. 5A is a graph illustrating the cell growth curve and the target protein concentration measured during the batch culture of the clones selected from the gs gene knockout HEK293 host cell introduced with the target protein by using MSX (0 µM, 25 µM, and 50 µM).

The present inventors further investigated whether or not the target protein production clones selected according to the concentration of MSX could affect the productivity and the growth rate in the serum free suspension culture. Particularly, the target protein production cell lines selected at different concentrations of MSX (Ab-MSX 0 µM, Ab-MSX 25 µM, and Ab-MSX 50 µM) were suspension-cultured in Ex-Cell® 293SFM medium (Sigma). When the cells grew to the exponential growth phase, the cells were sub-cultured under the same condition as the above in order for the cells to be adapted to the suspension culture until the cell growth rate recovered and reached the same cell growth rate as shown in adhesion culture. The target protein production cell line which had been adapted to the suspension culture was further cultured in the serum free medium via batch culture. The protein production and the specific production rate of each cell line were measured. After the cells were batch-cultured in the serum free medium, the single cell line displaying a high target protein production rate with increasing the MSX concentration was selected. At last, it was confirmed that the target protein productivity was increased (see FIGS. 5A and 5B).

As confirmed by the above results, in the HEK293_GS-KO host cell line of the present invention, GS protein was not expressed. Therefore, it can be efficiently used for the selection of the cell line demonstrating a high productivity of a target protein by introducing a gene encoding the target protein together with gs gene. The prepared protein production cell line can maintain the productivity even in the serum free medium environment, suggesting that a target protein can be produced with high yield in HEK293 cells.

Therefore, the gs gene knockout novel HEK293 cell line of the present invention can be efficiently used for the production of a target protein.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Confirmation of MSX Resistance of HEK293 Cell Line

The cell growth rate and the cell viability were investigated in the course of culture of HEK293 cell line with the addition of different concentrations of MSX.

Particularly, HEK293 host cells were inoculated in 50 ml of the glutamine-free EX-CELL® 293 SFM medium (Sigma), and also inoculated in the control medium supplemented with 4 mM glutamine. To the experimental group, MSX, the glutamine synthetase inhibitor, was added at the concentrations of 0 µM, 100 µM, 300 µM, 500 µM, and 1000 µM, respectively. The cell mixture was inoculated in Erlenmeyer flask at the density of 3×10$^5$ cells/ml, followed by suspension culture. 1 ml of the cell culture fluid was taken from each flask every 24 hours, followed by investigation of the cell concentration and the cell viability.

As a result, as shown in FIG. 1, GS protein was highly expressed in the HEK293 cell line, indicating that the HEK293 cell line had high resistance against MSX, the GS inhibitor (FIG. 1).

Experimental Example 1

Construction of gs Gene Knockout HEK293 Cell Line

Figure 2A:
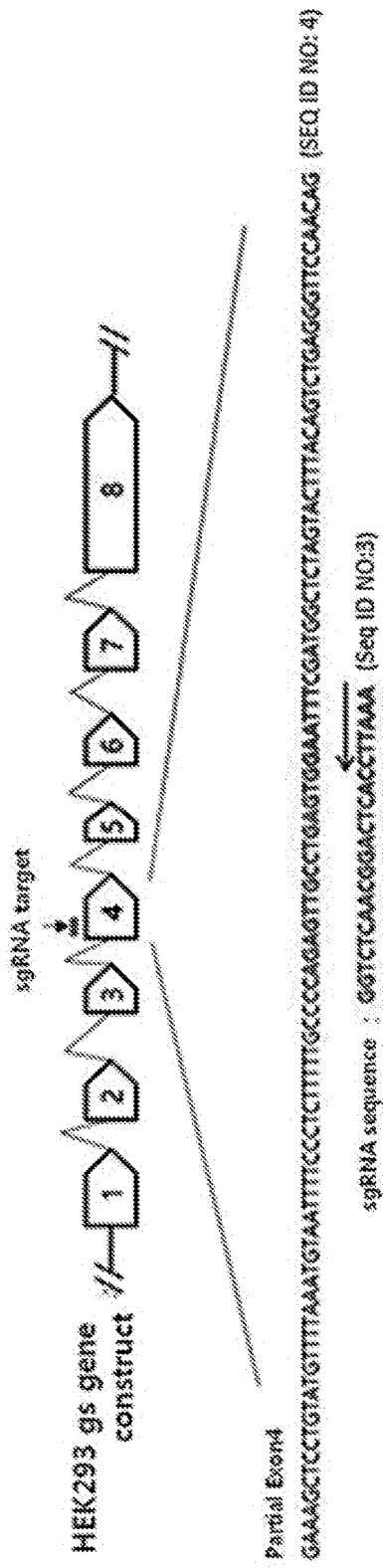
FIG. 2A is a diagram illustrating the gs gene structure in HEK293 cells and the target location of the CRISPR used herein; The exon of gs gene is indicated by the pointing box and the non-coding DNA is indicated by the full line. The sequence of the sense strand of the gene recognized by CRISPR is indicated by the red. The sgRNA adhering onto the corresponding sense strand (guide RNA) is presented under the target sequence and the direction of the said sgRNA is indicated by the black arrow.

To construct gs gene knockout HEK293 cell line, HEK293 host cells (ATCC, CRL-10852™) were first cultured in DMEM (Dulbecco's Modified Eagle's Medium, Gibco, Grand Island, N.Y., USA) supplemented with 1×GSEM (glutamine synthetase expression medium, Sigma-Aldrich, St. Louis, Mo., USA), 7% (v/v) FBS, and glutamine via adhesion culture. The adhesion-cultured HEK293 host cells were transfected with the vector encoding sgRNA 'GGTCTCAACGGACTCACCTTAAA' (SEQ. ID. NO: 3) targeting 'CCAGAGTTGCCTGAGTGGAATTT' (SEQ. ID. NO: 2) sequence of gs gene exon 4 and the vector expressing Cas9 protein by using lipofectamine 2000 (Life technology) (FIG. 2A). The cells were inoculated in 5 ml of the medium above in T-25 flask at the density of $4 \times 10^5$ cells/ml. 24 hours later, when the cultured cells reached 90% of confluency in the flask, 5 μg of sgRNA vector DNA, 5 μg of Cas9 protein vector DNA, and 20 μl of lipofectamine complex were added to the OptiMEM medium (Gibco), followed by culture for 24 hours. Exactly 24 hours after the addition of those vectors, cell culture was continued for 2 weeks in a 96 well plate for the selection of single cells. The selected single cells were cultured in a 24 well plate respectively in the conventional culture medium and in the glutamine-free medium (DMEM containing 1×GSEM and 10% (v/v) dFBS), during which cell growth was observed. The cells that did not grow in the glutamine-free medium were selected. Western blotting was performed with those selected non-growing cells, and as a result the cells that did not express GS protein were selected. Genomic DNA was taken from the selected cells which did not express GS protein, from which the sequence of gs gene exon 4 was analyzed. Gene mutation was observed in every allele of gs gene, and accordingly gs gene knockout cell line (HEK293_GS-KO) was selected. The wild type HEK293 cell line not-introduced with gs targeting CRISPR (sgRNA and Cas9 protein) was used as the control.

TABLE 1

| Name | Sequence |
| --- | --- |
| exon 4 target sequence (SEQ. ID. NO: 2) | CCAGAGTTGCCTGAGTGGAATTT |
| sgRNA (SEQ. ID. NO: 3) | GGTCTCAACGGACTCACCTTAAA |

Figure 2B:
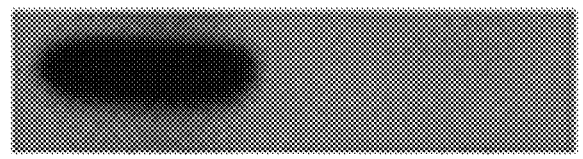
FIG. 2B is a diagram illustrating the result of the Western blotting showing that GS protein is not expressed in the gs gene knockout HEK293 host cell (HEK293_GS-KO) in which gs gene is knocked out by CRISPR; Control: the wild type HEK293 host cell not introduced with the CRISPR targeting gs gene.
Figure 2B:
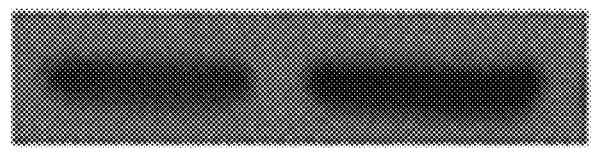
Figure 2C:
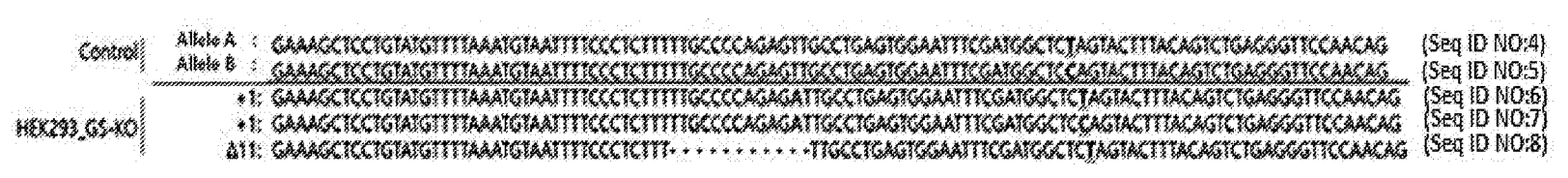

As shown in FIG. 2, the expression of 42 KDa GS protein was completely knocked out in the HEK293_GS-KO cell line (FIG. 2B), and gene mutation was observed in every allele of gs gene. Precisely, two types of mutations were observed in three homologous genomic sequences, wherein the addition of A was observed in two of those sequences and 11 nucleotides were deleted in the other sequence. The gene sequences are shown in Table 2 and FIG. 2C. The HEK293_GS-KO cell line was deposited at Korean Collection for Type Cultures (KCTC), Korea Research Institute of Bioscience and Biotechnology (KRIBB) on Feb. 17, 2016 [Accession No: KCTC12978BP, Human Embryonic Kidney 293 EBNA GS-KO (HEK293 cell line)].

TABLE 2

| Name | | Sequence |
| --- | --- | --- |
| Control | Allele A (SEQ. ID. NO: 4) | GAAAGCTCCTGTATGTTTTAAATGTAATTTTCCCTCTTTTTGCCCCAGAGTTGCCTGAGTGGAATTTCGATGGCTCTAGTACTTTACAGTCTGAGGGTTCCAACAG |
| | Allele B (SEQ. ID. NO: 5) | GAAAGCTCCTGTATGTTTTAAATGTAATTTTCCCTCTTTTTGCCCCAGAGTTGCCTGAGTGGAATTTCGATGGCTCCAGTACTTTACAGTCTGAGGGTTCCAACAG |
| HEK293_GS-KO | +1 (SEQ. ID. NO: 6) | GAAAGCTCCTGTATGTTTTAAATGTAATTTTCCCTCTTTTTGCCCCAGAGATTGCCGAGTGGAATTTCGATGGCTCTAGTACTTTACAGTCTGAGGGTTCCAACAG |
| | +1 (SEQ. ID. NO: 7) | GAAAGCTCCTGTATGTTTTAAATGTAATTTTCCCTCTTTTTGCCCCAGAGATTGCCTGAGTGGAATTTCGATGGCTCCAGTACTTTACAGTCTGAGGGTTCCAACAG |
| | Δ11 (SEQ. ID. NO: 8) | GAAAGCTCCTGTATGTTTTAAATGTAATTTTCCCTCTTTTTGCCTGAGTGGAATTTCGATGGCTCTAGTACTTTACAGTCTGAGGGTTCCAACAG |

Experimental Example 2

Investigation of Glutamine Dependency of gs Knockout HEK293 Cell Line

The adhesion-cultured HEK293 GS-KO cell line obtained in Experimental Example 1 and the wild type HEK293 cell line were adapted to the medium supplemented with glutamine and the glutamine-free medium, followed by measurement of the cell growth and the cell viability.

Particularly, DMEM with or without glutamine was added with 1×GSEM and 10% (v/v) dFBS, resulting in the preparation of each medium with or without glutamine. The wild type HEK293 cell line and the HEK293_GS-KO cell line were inoculated in 3 ml of each medium with or without glutamine in a 6 well flask at the density of $1 \times 10^5$ cells/ml. The cell concentration and the cell viability were measured in each well every 24 hours.

Figure 3:
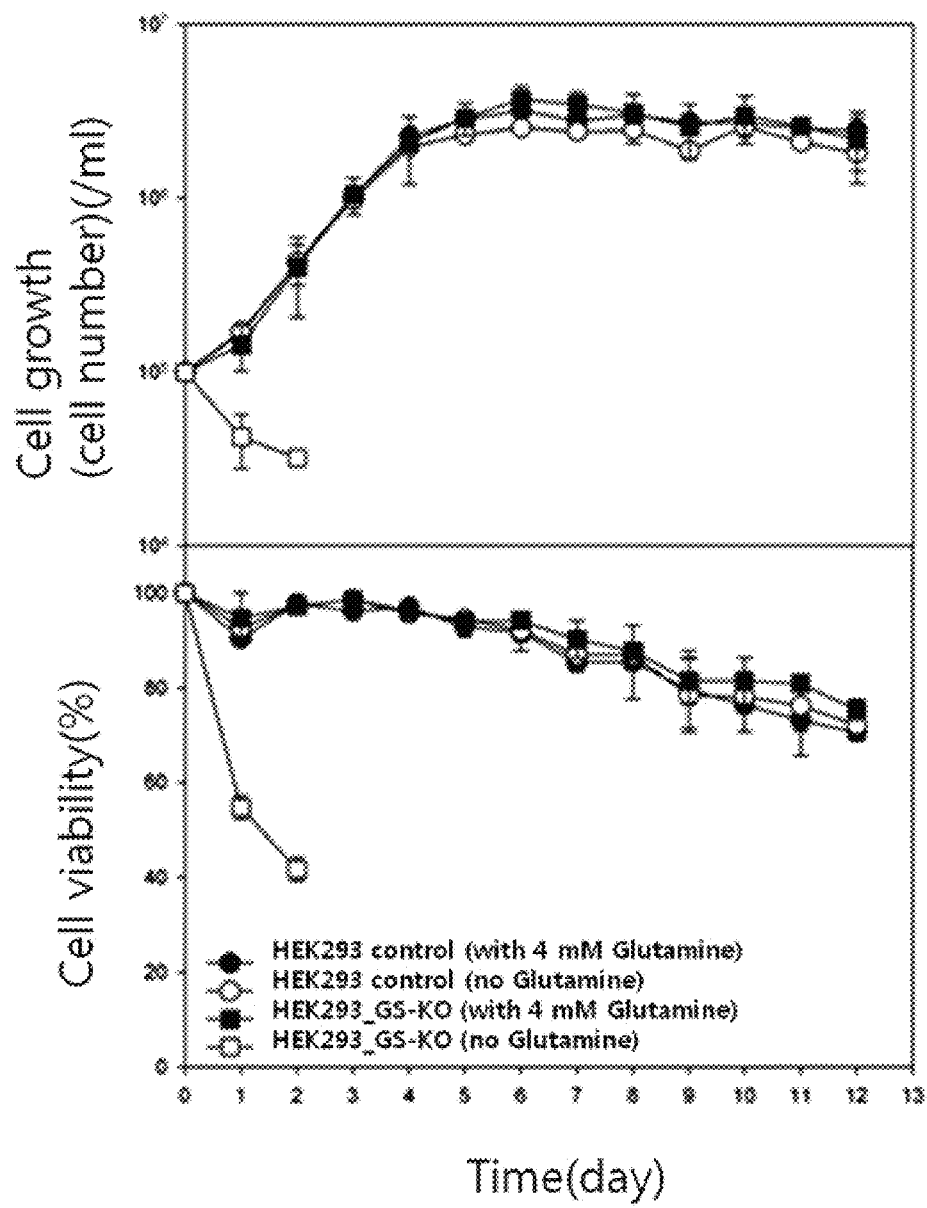
FIG. 3 is a graph illustrating the cell growth curve and viability of the gs gene knockout HEK293 host cell and the control which had been batch-cultured in the medium containing 4 mM glutamine and in the glutamine free medium.

As shown in FIG. 3, the wild type HEK293 cell line demonstrated a similar cell growth and viability either in the presence or in the absence of glutamine. However, the HEK293_GS-KO cell line did not grow in the absence of glutamine and the cell viability dropped rapidly under 50% on day 2, despite it maintained as normal cell growth and viability as those of the wild type in the presence of glutamine (FIG. 3). Therefore, it was confirmed that the HEK293_GS-KO cell line had glutamine dependency, which is the cell line did not grow normally in the glutamine-free medium because the expression of GS protein was knocked out.

Experimental Example 3

Production of a Target Protein Using the gs Gene Knockout HEK293 Cell Line

The following experiment was performed to confirm whether or not the gs gene knockout HEK293 host cell line obtained in Experimental Example 1 could be used for the production of a target protein.

First, the cells were inoculated in T-25 flask containing 5 ml of DMEM supplemented with 1×GSEM, 7% (v/v) FBS and glutamine at the density of $4 \times 10^5$ cells/ml. 24 hours later, when the cultured cells reached 90% of confluency in the flask, the vector containing a target protein gene mixed with liposome was additionally added to the gs gene knockout HEK293 cell line prepared in Experimental Example 1. 24 hours later, the selection marker protein (GS) inhibitor MSX was treated to the selection medium (glutamine-free DMEM supplemented with 1×GSEM and 10% (v/v) dFBS) at the concentrations of 0 μM, 25 μM, 50 μM, and 100 μM. The cells introduced with the vector were inoculated in the 96 well plate by 200 μl/well. The wild type HEK293 host cell line was also introduced with a target protein gene by the same manner as described above, followed by the selection from the 96 well plate. The cell concentration for the inoculation into the 96 well plate was determined by the concentration at which only one clone would survive after 3 weeks of selection period. To select the MSX resistant cell line (transformed cell line), the cells showing MSX resistance could be collected as a pool or prepared as each individual clone and herein the cell line was collected as an individual clone.

As a result of the cell line selection, as shown in Table 3, the wild type HEK293 cell line transfected with a target protein gene had to be inoculated one cell per each well in order to obtain one clone from each well and the cell survival rate was high in general. However, in order to obtain a clone, the gs knockout HEK293 cell line introduced with a target protein gene had to be inoculated at the density of 2000 cells per each well and the cell survival rate was low. Unlike the wild type HEK293 cell line, the HEK293 GS-KO displayed as low cell survival rate as 0.5% in the presence of 100 µM of MSX, so that this cell line was excluded in the next clone selection process.

[Table 3]

Selection condition of the target protein production cell line from the wild type HEK293 and the gs gene knockout HEK293 host cells using MSX

| Host cell line | MSX conc. (µM) | Inoculation conc. (cells/96 well) | Survival rate (%) |
| --- | --- | --- | --- |
| Wild type HEK293 host cell line | 0 | 1 | 27.1 |
| | 25 | 1 | 22.9 |
| | 50 | 10 | 28.1 |
| | 100 | 500 | 75.8 |
| HEK293_GS-KO Host cell line | 0 | 10 | 16.0 |
| | 25 | 2000 | 11.9 |
| | 50 | 2000 | 2.3 |
| | 100 | 5000 | 0.5 |

In the table above, "survival rate" was obtained by dividing the number of all the wells containing the cell by the number of the total inoculated wells.

The cells inoculated in a 96 well plate were observed under microscope and the medium was replaced every 5~7 days. About 2 weeks later, when a well was confirmed to have one clone growing at least 50%, the well was treated with trypsin (Gibco) to collect the cells. The collected cells were inoculated in a 48 well plate (500 µl). When the cells were grown in the well, the cells were inoculated again in a 24 well plate (1 ml). When the cells were fully grown in the 24 well plate, the cells were collected and inoculated in another 24 well plate containing 1 ml of culture medium at the density of $1 \times 10^5$ cells/ml. To quantify the production of the target protein, batch culture was performed for 6 days. On the $6^{th}$ day, the medium was collected and ELISA was performed with the target protein to measure the productivity of each clone. By the method above, 50 clones originated from the gs knockout HEK93 cell line were constructed each in the presence of 0 µM, 25 µM, and 50 µM of MSX. 50 control clones originated from the wild type HEK293 cell line were also constructed for comparison.

Figure 4:
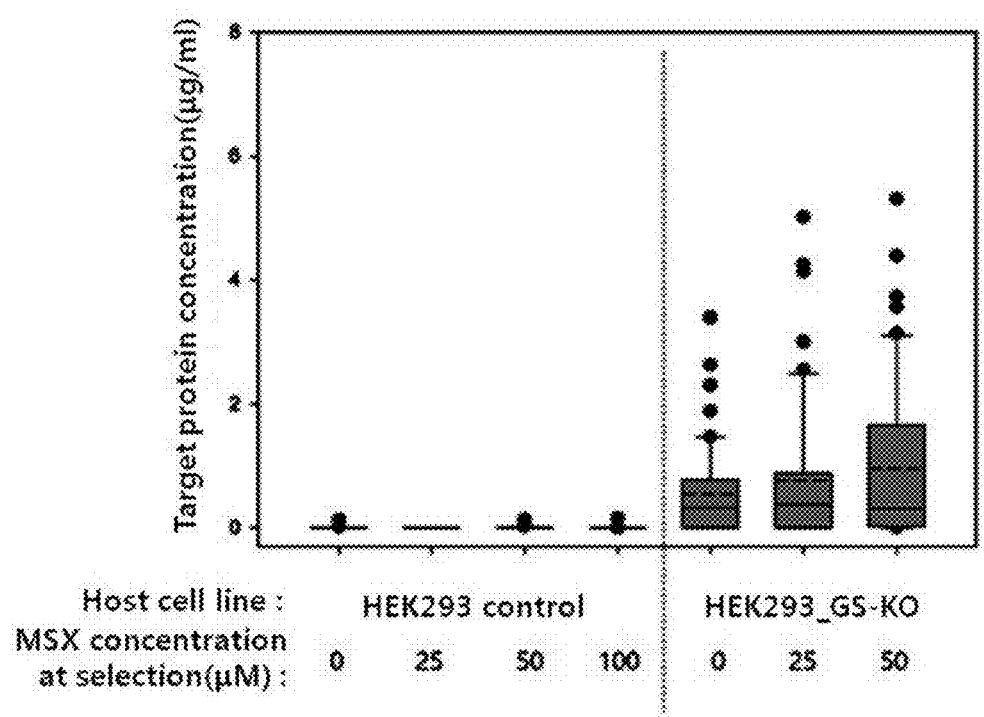
FIG. 4 is a graph illustrating the production of the target proteins (monoclonal antibody) in the 50 clones selected by MSX selection from the gs knockout HEK293 host cell and the control, which had been introduced with the target protein gene.

As shown in FIG. 4 and Table 4, those target protein production clones selected from the wild type HEK293 did not produce the target protein regardless of the concentration of MSX. Therefore, the selection efficiency of the protein production clone was 0% actually. However, the target protein production clones selected from the gs knockout HEK293 cell line did produce the target protein and accordingly the production efficiency was increased in proportion to the concentration of MSX. The protein concentration in the highly productive clone was also increased MSX dose-dependently as follows: 3.4 µg/ml in the presence of 0 µM of MSX, 5.0 µg/ml in the presence of 25 µM of MSX, and 5.3 µg/ml in the presence of 50 µM of MSX. In the gs knockout HEK293 cell line, endogenously highly expressed GS was eliminated, unlike in the wild type HEK293, so that gs could work efficiently in the MSX selection as a selection marker gene, resulting in the increase of the production cell line selection efficiency and the productivity of the same.

TABLE 4

Selection efficiency of the target protein production cell line from wild type HEK293 and the gs gene knockout HEK293 host cells using MSX

| Host cell line | MSX conc. (µM) | Selection efficiency (%) | High production clone/ 50 (total selected clone number) |
| --- | --- | --- | --- |
| Wild type HEK293 host cell line | 0 | 0 | 0/50 |
| | 25 | 0 | 0/50 |
| | 50 | 0 | 0/50 |
| | 100 | 0 | 0/50 |
| HEK293_GS-KO Host cell line | 0 | 16% | 8/50 |
| | 25 | 20% | 10/50 |
| | 50 | 36% | 18/50 |

In the Table above, "selection efficiency" indicates the portion of high production clones (those clones that could produce a target protein at least 1 µg/µl until the $6^{th}$ day) in 50 constructed clones at each condition.

Experimental Example 4

Investigation of the Target Protein Production in the Suspension Culture of the Clones Selected from the gs Knockout HEK293 Host Cell Line MSX was treated to the gs knockout HEK293 host cell line at the concentrations of 0 µM, 25 µM, and 50 µM, followed by the selection of target protein production clones. These clones (Ab-MSX 0 µM. Ab-MSX 25 µM, Ab-MSX 50 µM) were suspension-cultured in a serum-free medium. The viable cell concentration, the protein productivity, and the specific production rate were measured.

Particularly, the adhesion-cultured cells were inoculated in 25 ml of glutamine-free EX-CELL® 293 SFM (Sigma) supplemented with 1×GSEM and different concentrations of MSX at the density of $5 \times 10^5$ cells/ml and then suspension-cultured in Erlenmeyer flask. Three days later, when the cells reached the exponential phase, sub-culture was performed under the same condition as the above. On the third day of the sub-culture, suspension-culture was performed until the cell density reached $1 \times 10^6$ cells/ml, leading to the adaptation of the cells in the serum free suspension culture. The target protein production clones (Ab-MSX 0 µM. Ab-MSX 25 µM, Ab-MSX 50 µM) adapted to the serum free suspension culture were batch-cultured and the cell growth and the target protein productivity were measured.

Figure 5B:
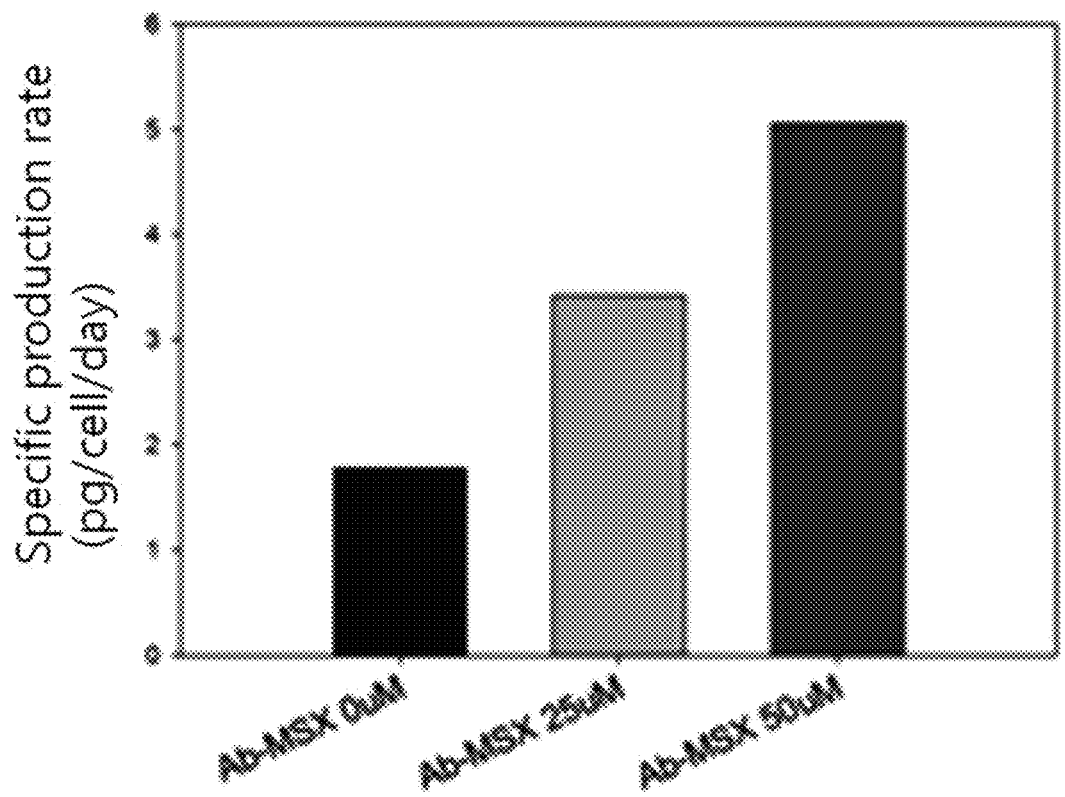
FIG. 5B is a graph illustrating the unit time and the specific production rate per cell measured during the batch culture of the clones selected from the gs gene knockout HEK293 host cell introduced with the target protein by using MSX (0 µM, 25 µM, and 50 µM).

As a result, the target protein production clones constructed from the gs knockout HEK293 host cell line could be able to produce the target protein as much in the serum-free suspension culture condition (FIG. 5A) and the specific production rate was increased MSX dose-dependently (FIG. 5B). Therefore, it can be said that the gs knockout HEK293 host cell line can increase the selection efficiency of the production cell line in the course of the production cell line selection process using GS/MSX system and the productivity of the target protein by the cell line. The production cell line constructed thereby can be easily adapted to the serum-free suspension culture and accordingly be useful for the culture in a large scale, indicating that the cell line can be efficiently used for the high concentration target protein production in HEK293 cells.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

All publications referred to herein are incorporated herein to the extent not inconsistent herewith. References cited herein are incorporated by reference herein in their entirety to indicate the state of the art as of their filing date and it is intended that this information can be employed herein, if needed, to exclude specific embodiments that are in the prior art.

What is claimed is:

1. A glutamine synthetase (GS) knockout transgenic HEK293 cell line comprising one or more mutations of the nucleotide sequence of SEQ ID NO:1 within the 4$^{th}$ exon of the gs gene.

2. The GS knockout transgenic HEK293 cell line according to claim 1, wherein the cell line is the transgenic HEK293 cell line on deposit at the Korean Collection for Type Cultures (KCTC) under accession number KCTC12978BP.

3. The GS knockout transgenic HEK293 cell line according to claim 1, wherein the one or more mutations is an addition of an adenine nucleotide to the nucleotide sequence of SEQ ID NO:1 or a deletion of 11 nucleotides from the nucleotide sequence of SEQ ID NO:1.

4. The GS knockout transgenic HEK293 cell line according to claim 1, wherein the cell line is originated from HEK293 cells.

5. The GS knockout transgenic HEK293 cell line according to claim 4, wherein the HEK293 cell is selected from the group consisting of HEK293E, HEK293.sus, and HEK293T.

6. A method for producing a target protein comprising the following steps:
   1) constructing a transformed HEK293 cell line manipulated to express a target protein by introducing a vector containing a gene encoding the target protein into the GS (glutamine synthetase) knockout transgenic HEK293 cell line of claim 1;
   2) culturing the cell line prepared in step 1); and
   3) separating and purifying the target protein produced in the cell line of step 2).

7. The method for producing a target protein according to claim 6, wherein the GS knockout transgenic HEK293 cell line of step 1) is the transgenic HEK293 cell line on deposit at the Korean Collection for Type Cultures (KCTC) under accession number KCTC12978BP.

8. The method for producing a target protein according to claim 6, wherein the target protein is selected from the group consisting of soluble TNF receptor, soluble IL-4 receptor, soluble IL-1 type II receptor, soluble CD40 ligand, CD39, CD30, CD27, TEK/ORK, IL-15 receptor, GM-CSF, RANKL, RANK, TRAIL, soluble TRAIL receptor, tissue plasminogen activator, factor VIII, factor IX, apolipoprotein E, apolipoprotein A-I, IL-2 receptor, IL-2 antagonist, alpha-1 antitrypsin, growth hormone, insulin-like growth factors, parathyroid hormone, interferon, monoclonal antibody (mAb), erythropoietin (EPO), thrombopoietin (TPO), and Fc containing fusion protein.

* * * * *

SEQUENCE LISTING

```
<160> NUMBER OF SEQ ID NOS: 9

<210> SEQ ID NO 1
<211> LENGTH: 31
<212> TYPE: DNA
<213> ORGANISM: Artificial
<220> FEATURE:
<223> OTHER INFORMATION: primer

<400> SEQUENCE: 1
tttttgcccc agagttgcct gagtggaatt t                              31

<210> SEQ ID NO 2
<211> LENGTH: 23
<212> TYPE: DNA
<213> ORGANISM: Artificial
<220> FEATURE:
<223> OTHER INFORMATION: gs gene 4 exon target

<400> SEQUENCE: 2
ccagagttgc ctgagtggaa ttt                                      23

<210> SEQ ID NO 3
<211> LENGTH: 23
<212> TYPE: DNA
<213> ORGANISM: Artificial
<220> FEATURE:
<223> OTHER INFORMATION: sgRNA Artificial

<400> SEQUENCE: 3
ggtctcaacg gactcacctt aaa                                      23

<210> SEQ ID NO 4
<211> LENGTH: 106
<212> TYPE: DNA
<213> ORGANISM: Artificial
<220> FEATURE:
<223> OTHER INFORMATION: gs gene allele A Artificial

<400> SEQUENCE: 4
gaaagctcct gtatgtttta aatgtaattt tccctctttt tgccccagag ttgcctgagt    60
ggaatttcga tggctctagt actttacagt ctgagggttc caacag                 106

<210> SEQ ID NO 5
<211> LENGTH: 106
<212> TYPE: DNA
<213> ORGANISM: Artificial
<220> FEATURE:
<223> OTHER INFORMATION: gs gene allele B Artificial

<400> SEQUENCE: 5
gaaagctcct gtatgtttta aatgtaattt tccctctttt tgccccagag ttgcctgagt    60
ggaatttcga tggctccagt actttacagt ctgagggttc caacag                 106
```

<210> SEQ ID NO 6
<211> LENGTH: 107
<212> TYPE: DNA
<213> ORGANISM: Artificial
<220> FEATURE:
<223> OTHER INFORMATION: HEK293_GS-KO 1 Artificial

<400> SEQUENCE: 6

```
gaaagctcct gtatgtttta aatgtaattt tccctctttt tgccccagag attgcctgag    60
tggaatttcg atggctctag tactttacag tctgagggtt ccaacag                 107
```

<210> SEQ ID NO 7
<211> LENGTH: 107
<212> TYPE: DNA
<213> ORGANISM: Artificial
<220> FEATURE:
<223> OTHER INFORMATION: HEK293_GS-KO 2 Artificial

<400> SEQUENCE: 7

```
gaaagctcct gtatgtttta aatgtaattt tccctctttt tgccccagag attgcctgag    60
tggaatttcg atggctccag tactttacag tctgagggtt ccaacag                 107
```

<210> SEQ ID NO 8
<211> LENGTH: 95
<212> TYPE: DNA
<213> ORGANISM: Artificial
<220> FEATURE:
<223> OTHER INFORMATION: HEK293_GS-KO 3 Artificial

<400> SEQUENCE: 8

```
gaaagctcct gtatgtttta aatgtaattt tccctctttt tgcctgagtg gaatttcgat    60
ggctctagta ctttacagtc tgagggttcc aacag                               95
```

<210> SEQ ID NO 9
<211> LENGTH: 14114
<212> TYPE: DNA
<213> ORGANISM: Homo sapiens

<400> SEQUENCE: 9

```
gtaaaactat tccccgtgaa ggcggcaggg cagaggtcca gggcgggctt tgctgggagc    60
ctcgggaccc cgggttgggg gccgtggggc ggcacctggc gagctggcgg gtgggcggcg   120
agccgaggct tcccggcctg gcggcaactc gcccctctgc cctcagccct cccggctccg   180
ctcccttccc ccacgccgcc ctgccccctcc ccacgccccc tttctctttc tttctttctt   240
tcccagttcg cttgccccca cccagcggc gcccgccggg ctcctcgccc aatggccgcg    300
gggcccggga ccgcatcagc tgatcggccc gggctcctgg ccgctgggag ccaatcaggg   360
caccgggggc ggccccgggc cgcggataaa gggtgcgggg ctgctggcgg ctctgcagag   420
tcgagagtgg gagaagagcg gagcgtgtga gcagtactgc ggcctcctct cctctcctaa   480
cctcgctctc gcggcctagc tttacccgcc cgcctgctcg cgaccaggt aagccccggg    540 acggcccggt gtcacgcaag cgaggcgcgc cgccctgct acccgcgag gcgcgccgcc    600 cagcctcttt tttcggctgc ctgccccctcc agtcccagcc ctacgctgcg gcctctccgg   660
cccatgcctg agatccggca tgagtgctcc tcccgcgtgc ttccgccgct ggtggcttgg   720
acccgtcggg gctggcgctg gtggggcgcg cccttggcca ggctctggga agggcggggt   780
gagttgtttt gatcttcttt tcactacttg cggccgaagc gccgcccctg gaggccgttg   840
ggccggcctg cgccctgggg ctcgcagtgg tttgtttgcg ctgtggatgg agtggcggtg   900
```

```
cggtcccctg tggagcgcaa acaaggcgct tggttggcgc gggcgcctgg ctgccttcct    960
cgtggtgggg ccttcggagc aatcgtcctg gttctggcga tggttgagac gcctcgattg   1020
cggcgtgtaa cggtgagcgt tgtttgggcg gccggctccc gcctcggggt cccggggggcc  1080
ttccaatgtg accgaacaat ggagagcccg ggcctcggcg cagtcagtgg agaagccggt   1140
ccgggcggag gcagcagcag cgcgcagtcc ctacggcctg cgcccccacc ctcccccgga   1200
cccccccaacc cctcggcggc agggtatggc cacctccgtg aggccctgag attcggacgg  1260
gggcccgagg ggcagggcgc ccactttagg gacatttcag tgggaagggg ctgctctcaa   1320
agtggataat tataactccc tcgggggcgg gaagcgggga tcctccccca gccgcaagtc   1380
cacgaagaaa gcaacgaatg aaaattatga agacaacgag aagtcagact cctccgggtc   1440
gcgctccagc tgcttcggct tcgtcgccta ctctgtgaac tccggggaga gatctcgagt   1500
caagattaag accttaaccc accaacctgc ctgttcggac accccccggg ccggccgctg   1560
tctgtcccct tctccatcgc cctctcccag aaagctccgg tgcttggacc agctagagtc   1620
tgagaaagag gagaggcgcg aacgccactc caaaaagaga agggttaaag agggcaaccc   1680
taacgatacg cttgactttc tgtgctgggt gtgagtgagg gggcagggag gacgaccccg   1740
gagttggtgg gagctgcaga aactgctgaa aacttcagaa tccatttccc ccacgtaaac   1800
ttggcaccgc agcagcagca gttgatagag tggcactagg ctgctggcat gcaactcggc   1860
tcacggaaaa gagcaagaga tccgaaactg aggcttagga caaagtgtgc atgatattgg   1920
tggtgtaaca tgttggagag gacagccgag aaattgggtt gtaggttttt tttttttgtt   1980
ttccgacaga gtctctatct gttacccagg ttggagtgca gtggtgcaat ctcccggctc   2040
actgcaacct ctgcctctgg ggttcaggcg attctcctgt gtcagcctcc cgagtagctg   2100
ggattacagg cgtgcacaac cacgcccggc taattttttgt attttttagta gagacgggag  2160
tttcatcgtg ttggccaggc tggtctcgaa cttttgtacct caggtgatct gcccgcttcg   2220
gtgggttgta gcttttagcg ggagctaaag ggttctggga tggaggtggg aagtaggatt   2280
tggccggctg agtcttctag aggcaatatt ggggtgttgg tcttccccaa ggggaagggt   2340
ggtgaggctg agggagaagc agttatgttt tcagctgggc aaacatggac ggttgcccgt   2400
agaaactttg ccactgtact tcagaacgtt gccctagtcg ttggaggaga acaatgtgtt   2460
ccctttctag ccaccctggt ccacggaggg aggaggagag gagagaatgt ttcctcttcg   2520
gctgttgtgg cttgagagtt tctcttcttt cggaggtttt gtggtagtgg ctggcagtta   2580
ttagtatgcc tcatggcttt taaatttcca gatcttttg atttagaagt ggaaatttcc    2640
taattacttg acaagtcttg tagaattcca taatgttgtg attcttgccc actatcttaa   2700
gtgagacttt gcatgagacc tatggaaatt atggcagcat tcccctttaga atctggcttg  2760
aatcagcttt tgtgtaggaa actgctagcc ttctaaaaaa atatattgta accttgtttc   2820
atcctcaaat ctaaatgtgt aatgagtttt cttttggtgg ggaggggcgg tgggtttgag   2880
ttaagaccac agctaggatg aaagacaaag agaaaaacaa actgtggaag ccaagcctgt   2940
tctgtggctg gattttactt atattggaag aagttctatg ttttgtaaat ttgtgtattg   3000
gttttgattt gtttcctctg atagtttagt atttggatag tttagtgtta acctcagcta   3060
cactgaagga atagacctta gtcctcacaa gtataagttc tagcttggaa gcctgggttc   3120
tgcagtagct gtgaacttaa gcctgtgag ctcaggatg cagaggcatt gagttactac      3180
caagggcctg atctttctt tagcaggcat ctgtgttaat tgtttcaaaa ggtggtgatc    3240
```

```
agttttacag cctattataa aggagatttt tgcctactat aaaactaatc cccctgaaag    3300
agtgagtaaa cataactttt tgtgtgttga cttccacaag ggaaggagtt ggcacttaca    3360
ctctgacttt tgattcagtc gtccttcttg agccattttt gcagggggatc agtttggagt   3420
gggcgttaac aatgttattc ttttttttctt ctccagaaca ccttccacca tgaccacctc   3480
agcaagttcc cacttaaata aaggcatcaa gcaggtgtac atgtccctgc ctcagggtga    3540
gaaagtccag gccatgtata tctggatcga tggtactgga gaaggactgc gctgcaagac    3600
ccggaccctg gacagtgagc ccaagtgtgt ggaaggtgag acagcaatgt ggagtggagc    3660
acatgctggg tgggatctgc agaggggtgg gcagcagcct ttgactcagc ctctggatta   3720
ggcctctttc ttctgtttgt aaaggttttc taaggcaggg cttttcagac tttattcagt   3780
caacattaag ctcctacact gcctcaaagc agagcgacga tggaacccct tatttcaatg    3840
gaattgtgca cgtaggccag tgtattgaag aaaaactaag tctggtttat ggagagttgg    3900
catgggcctt agaggttgcc gacctggaca tccccactta gctggctcta aggcaccctc    3960
agaaaaccac tgctctaacc tgagaatgcc atctagttta caaactctta gaaaactgtg    4020
tttaatactc atatcactgg cttctagatg tgaagcaaat gctctacaat ggttttaaa     4080
taggactaat ttttagttga tgccactttt ggaaattctt aaactaattg cgtatccctc    4140
taggagctac agttagatta tagttgtgac cttcattttt cagtctagaa caagccatag    4200
tcttccctct tctggaaagg ggccagagga aagtatcata tcctacctag tttagggtag    4260
tttacttttc cttttttgagt aagtgaatga tcataataca aagcctatat tgtgtacttg   4320
ctatgtggca gatgatagtg cacagacact gaagatacaa agtgagagtc tcgtctctgc    4380
cttcagagaa ctcagtcagc tagagagacc aagcagcctt caaaacagtg ggaaaggtgg    4440
ataggtgata agggagcatc ctagagtaag tcatcctgct agtcgtctgt tccctcatct    4500
ataaaataag gacataactt gccagaatac actgggggca taagaaggat gcaacacatt    4560
acctaatgga agaatcagaa tccttcacta tctcaatatt ttaagtgatt gataggatgg    4620
tagtgataac agaatgcttc agcttgtctc ctggaagaca tttgggaagg gagtatctga    4680
tatatttctt ttaaggaatt ggtacaatgg tcttacttgg aactcaaata ggaagggcta    4740
taagatcagg tacaggtgcc agggtataca tattaatgat ggcatttata ccttaatgaa    4800
ttcctggaaa agagatattt agagatggga aggtgagtga agggctggct gtatttgcat    4860
tgcttggaaa gctcctgtat gttttaaatg taattttccc tcttttttgcc ccagagttgc   4920
ctgagtggaa tttcgatggc tctagtactt tacagtctga gggttccaac agtgacatgt    4980
atctcgtgcc tgctgccatg tttcgggacc ccttccgtaa ggaccctaac aagctggtgt    5040
tatgtgaagt tttcaagtac aatcgaaggc ctgcaggtgt gttatagcac agctatggat    5100
accccctcctc aatctgtgaa tgctgtgaag gggagggaga agacattctg aaatcagcat   5160
tgggaagact aggcaatttc agcactattt taagaatctg agtgattctt ttccctgaac    5220
ttctgctttg aggaagagat aatatggccc atctttctat ggtcttctct gttggttgca    5280
taaaatagca ttggatttgt ccagatctgt ttgccggtct tggagtcccc agtaacagcc    5340
ttcctgcctg gaatgtaggc caggacaaat gtaaaccaat ggacaaatgt ttctcaaaaa    5400
ttatagaatg gctccaagtg cctgagaaat gaagaataaa tctgacaacc agaagcagct    5460
gtcttgtgaa tagagggtta agtgcctggc atttggtgct tgggaggtgg ccagaatgca    5520
gataaggtga aagttgccct gttctaaatc cactcccatg tgcttggtt gtaactgagt     5580
ttagttaaaa ctgaagtctt tcagagtctt cctacagatg tacaattaac agcttctctc    5640
```

-continued

```
atttttctga ctcggtgatc ccaagaaggc ctatactggg tcagttcata ccatagtgca    5700
cacctcagtt gtatagaatc caaggactat tctcccatca gcatcggtat tcagcatcta    5760
tgtctttaga tccctgatgg cgtattattg actctttttt ctagagacca atttgaggca    5820
cacctgtaaa cggataatgg acatggtgag caaccagcac ccctggtttg gcatggagca    5880
ggagtatacc ctcatgggga cagatgggca ccccttttgt tggccttcca acggcttccc    5940
agggccccag ggtaagtctc cttgggttag aggtgaaatt cccagaagtg tctaactgtg    6000
caggaatgcc ccttcccagg gatgggaatg actttcagaa tcaagaagca aaataataca    6060
gtaaaggcga aacagccctc acatcaccaa agtccaaaaa tggatatgaa tatataaagt    6120
aaggttttag ggggaacgtt tggccccact gaagctgtgg tgaagaggaa ctcccctatt    6180
gcccctcccc tgccccgcac ctgcagatga aggcaaggat agtgattcaa gagggcaagg    6240
cttaagggcc ttctgatctc tgactttggg attctctgga tttcttgact cttagtgttt    6300
tgtcctgatg cttctgtagg tccatattac tgtggtgtgg gagcagacag agcctatggc    6360
agggacatcg tggaggccca ttaccgggcc tgcttgtatg ctggagtcaa gattgcgggg    6420
actaatgccg aggtcatgcc tgcccaggta agtatagctc caatccatca atgaagaagg    6480
gtaggtaggt gtacatagga cttttgctag taagggctgc tgatacacca ctcactaacc    6540
caaaacctaa gaacgggttg gagtacaggt gagaagagaa caggtttagg agattctgag    6600
ttggagtgag cagttagctt tgttttaatg ccaagcttc tcgtttctag tgggaatttc    6660
agattggacc ttgtgaagga atcagcatgg gagatcatct ctgggtggcc cgtttcatct    6720
tgcatcgtgt gtgtgaagac tttggagtga tagcaacctt tgatcctaag cccattcctg    6780
ggaactggaa tggtgcaggc tgccatacca acttcagcac caaggccatg cgggaggaga    6840
atggtctgaa gtgagtacct tctgctgggg ccatctttaa tctcctgtgg cagaaaactt    6900
gggaggagac ttagcaatct ctcagcaaag tctcctttgc aggatgactt gcaaatattt    6960
gccaaagatg agtaaacttg acttctcagt ctggacgtac tttaggtgtt gacacttgcc    7020
ttcacattct ctcatttgt tcctatttga aaaataccaa ataatacttc tgattcacag    7080
tgataaatat ttgttataat ttatataata tatattagtc atatatcatt atataaatat    7140
atatcgatat atatatttgt gacatatgtc atggtgacag ggaaaagttg acaaattcat    7200
gcatttgaaa atcttttaga actaaattag taacaataca ggcatgtgga taagcttaat    7260
gcttatgagg gggagaaagt ttcaaatgat tagtcttttc aacaaacagt aactttgtac    7320
tgcttgtcgg gcactgttct caccactgag acacacaggt aagaagatgc agccactgcc    7380
ctcatgaagt atttgttcta ctggtatcat attttggtgc acttcattct tggctccata    7440
cctggagaca aggttggact gccatctttt ctgtttactc taggtacatc gaggaggcca    7500
ttgagaaact aagcaagcgg caccagtacc acatccgtgc ctatgatccc aagggaggcc    7560
tggacaatgc ccgacgtcta actggattcc atgaaacctc caacatcaac gacttttctg    7620
ctggtgtagc caatcgtagc gccagcatac gcattccccg gactgttggc caggagaaga    7680
agggttactt tgaagatcgt cgcccctctg ccaactgcga ccccttttcg gtgacagaag    7740
ccctcatccg cacgtgtctt ctcaatgaaa ccggcgatga gcccttccag tacaaaaatt    7800
aagtggacta gacctccagc tgttgagccc ctcctagttc ttcatcccac tccaactctt    7860
ccccctctcc cagttgtccc gattgtaact caaagggtgg aatatcaagg tcgtttttt    7920 cattccatgt gcccagttaa tcttgctttc tttgtttggc tgggatagag gggtcaagtt    7980
```

```
attaatttct tcacacctac cctccttttt ttccctatca ctgaagcttt ttagtgcatt    8040
agtggggagg agggtgggga gacataacca ctgcttccat ttaatggggt gcacctgtcc    8100
aataggcgta gctatccgga cagagcacgt ttgcagaagg gggtctcttc ttccaggtag    8160
ctgaaagggg aagacctgac gtactctggt taggttagga cttgccctcg tggtggaaac    8220
ttttcttaaa aagttataac caactttttct attaaaagtg ggaattagga gagaaggtag    8280
gggttgggaa tcagagagaa tggctttggt ctcttgcttg tgggactagc ctggcttggg    8340
actaaatgcc ctgctctgaa cacgaagctt agtataaact gatggatatc cctaccttga    8400
aagaagaaaa ggttcttact gcttggtcct tgatttatca cacaaagcag aatagtattt    8460
ttatatttaa atgtaaagac aaaaaactat atgtatggtt ttgtggatta tgtgtgtttt    8520
gctaaaggaa aaaaccatcc aggtcacggg gcaccaaatt tgagacaaat agtcggatta    8580
gaaataaagc atctcatttt gagtagagag caagggaagt ggttcttaga tggtgatctg    8640
ggattaggcc ctcaagaccc ttttgggttt ctgccctgcc cacccctctgg agaaggtggg    8700 cactggatta gttaacagac aacacgttac tagcagtcac ttgatctccg tggctttggt    8760
ttaaaagaca cacttgtcca cataggttta gagataagag ttggctggtc aacttgagca    8820
tgttactgac agagggggta ttggggttat tttctggtag gaatagcatg tcactaaagc    8880
aggccttttg atattaaatt ttttaaaaag caaaattata gaagtttaga ttttaatcaa    8940
atttgtaggg tttctaggta atttttacag aattgcttgt ttgcttcaac tgtctcctac    9000
ctctgctctt ggaggagatg gggacagggc tggagtcaaa acacttgtaa ttttgtatct    9060
tgatgtcttt gttaagactg ctgaagaatt attttttttc ttttataata aggaataaac    9120 cccacctta ttccttcatt tcatctacca ttttctggtt cttgtgttgg ctgtggcagg    9180
ccagctgtgg ttttcttttg ccatgacaac ttctaattgc catgtacagt atgttcaaag    9240
tcaaataact cctcattgta aacaaactgt gtaactgccc aaagcagcac ttataaatca    9300
gcctaacata agatctctct gatgtgtttg tgattcttc aaatccctat gtgccattat    9360
atttctttat ttcctaaaac aggcaaaata agctcaagtt tatgtactct gagtttttaa    9420
aacactggag tgatgttgct gaccagccgt ttcctgtacc tctctaagtt gggtatttgg    9480
gacttaaggg attaagtttt tcacctagac ttagttacac acaatcttgg catttcctag    9540
cctagaggtt tgtagcaggg tacaagcccc actcctcccc cttcctttgc tcccctgagt    9600
ttggttttgg cttaccataa cattgttttg accattccta gcctaataca atagcctaac    9660
ataatgtaag attaactggc tttacgattt ctattctctg ctctcagtga taagaaacaa    9720
atattagcta ccctgctacc ctggttgaag ccttccaagg ctggctatgc cctaggcatg    9780
ggctcatcct tgggtgtatc ttgccttgca ggaagaccag tggaccgatt gtgattctca    9840
aaagctctgt gttgtcacct gtgcccttgc cccttgctct tatcttggtc cgtgtatctg    9900
ggagttcttc caccttatct tggccaattc ctaccttcgt tcattcctca tgaggttggg    9960
taaaagctcc ctccggctcc catgatgctg tgcatatacc tagcaaaaag caattattgg   10020
acacattgga gtgcaatatt attaatagca ttaatactac taataatgtg ggcaatagtg   10080
attgttttta aaaggcagta tactcttacc agtgcgaggt agctggggcc tgtgatagtt   10140
tttagagata agttcttcag gcaactgtgt attttacact agtcaagtaa tcctagatat   10200
ccgtggtttt tcttaagaaa gttggctcgt aatatgattt aatattcaaa gtagagtcat   10260
ctacctatta gcttgctggc gtggtcctag tttatgcctg tttcagcatg attgttgagt   10320
accctgtttc atccttagca ttttcttgat tttgttgtta aatgatgtat acccttattt   10380
```

```
ccattgaatc tgtgcttcca ccccccccaac tgaagttgtc ttcccttttgc ttggccaccc   10440 ttacagcctc ttggatggtg tatcctacag tgtaagcact aaactgaaga ggcagtgacc   10500
tgagcacttt ggattttgtt cattgtaatc aattccatga caaaatgatt gcatgagaag   10560
gaattttaaa ttcataggat cagaatttag gtgaaaacaa ccagcatatt tgtttcttca   10620
ccctctcacc tagaattagc tttgacctac aggtcacagt gcaatcccct tgtatttcta   10680
aggtgttttt tatagttcat ttgcagacaa tgggttatgt gataactttt atcagtgata   10740
gattaaacag aataatgacc aagctttcaa ccttaaggag tcaggccagt atttacaaaa   10800
ggaggtctcc atgaactcct taaatatgag ttcccctaat atcatcttgc caggtactaa   10860
ataacaactg atagcacaag ctataggaa tttgaaagaa ttccatggat gggtgttgtc   10920
tagggccttt tgttgttttt gagacgggt ctgactctca cccaggctgg agtatagtgt   10980
ggcgcaatct tggctcactg caacttctgc ctcccagatt caagcgattc tcctgcctca   11040
gcctcccaag tagctgagac tacaggtgtg caccaccatg ctcagctaat ttttgtattt   11100
ttagtacaga tgggtttca ccatgttggc caggctggtc ttgaactcct gatctcccaa   11160
agtgaggtct tgaactggtc ttgaactcct ccacctccca aagtgctggg attacaggcg   11220
tgagccactg cacccggcct agggccatgt aaaaagccag atctgtgctg ctgtctgtgt   11280
agaagggtag acaagtggat gagaagttcc tgaactattc ttggcccttt taccactaag   11340
tgaaagtaac ttgctgcccc aaagaaagat gtctcatcat tcgacaggac tttctagttg   11400
aacttcatga aagcaagaga tcctgttttt cttgctcacc actgtatctt gagacctgtt   11460
gtagtgcctg caatacttat ttaataagtt attttttaagt atcagttttg tgagctttaa   11520
ctctatgagg tctttgttgt ttgactgtat tttaactctg gccatgacag caagacaaag   11580
ttccattttt attgagctta aaaagaatca aggccaggtg aagtggctta cgcctgtgat   11640
cccaacactt tgtgaggctg cagcaggagg atctcttgag cccaggagtt tgagaccgtt   11700
ctaggcaatg tagtgaggtc cagactccac aaaataattt tttttttaaat tgcacgcctg   11760 tagtctcagc tatcaggagg ctgagatggg aggatgactt gagcccagga aattgaagct   11820
gcagtgaatt gtgattgcac cactgcactc cagcctgggt gacagatcaa gaccttgcct   11880
aaacaaaaca aaacaaacaa aaccccaaaa aacaaattga aaatgttgat tctttttact   11940
acaaacatta tggcagcact aaaaacttcg tgggagtgta ctgtggaaaa tagtgtactt   12000
aattaattct cattgtaatc aggctaccaa gagccttgtg ttgctttaag agttataact   12060
gccaggcaca gtggctcatg cctataatcc cagcaccttg agaggccgag gcaggtggat   12120
cacctgagat cgggagtttg agaccagccg ggccaatatg gtgaaacaag ctgtgtctct   12180
actaaataca aaaaattagc cgggcgtggt ggcacatgcc tgtaatccca gctgcttggg   12240
agactgagac aggagaattg cttgaacctg gaaggcggag gttgcagtga gctgagattg   12300
caacattgta ctccagcctg gcaacaagag ggaaactcc atctcaaaaa aaaaaaaaa   12360 gttgtaactg aggctgggca tggtggctca tacctgtaat cccagcactt tgaaaagccg   12420
aggcaggtag atcacttgag ctcagaagtt cgagactagc ctgggcaaca tgacaaaacc   12480
ccatctctac aaaaaatacg aaaaattagc tgggcgtggt ggcatgcacc tgtagtccta   12540
gctacctggg aggctgaggt gggaagatta cttgaagctg cagtgagcca tggttgtgcc   12600
actgccctcc agtctgggca acaaagtgag accctgtctc aaaaaaacaa aaaaaatta   12660 taactgatgt aaactggcag tttaggctgg gtgtggtggc tcaagcctgt aatcctagca   12720
```

```
ctttgggagg ccaaggcagg tggatcacct gagttcagga gttcgagacc agcgtggcca   12780
acatggtgaa accttgtctc tattaaaaat accaaaatta gcaagatgtg gtggtgggtg   12840
cctataattc cagctactca ggaggctgag gcaggaggat cgctggagcc agggaggcag   12900
aggttacagt aagcaaagat cactccactt cactccagcc tgggcaaaag agtgagacat   12960
atcaaaaaat aaacaaataa ataaataaat aagtggcagt tcatcattta actccaaaga   13020
ctttgcgtac atttctactg aaaacaatct gagctgatta gaaccctgcc attttatagc   13080
ctttagctcg atctccgacc gttcatttaa aaaaattcta cttcaggccg ggcatggtgg   13140
ctcaagcctg taatcccatc actgtaggag gccaaagtgg gcagatcact taaggtcagg   13200
agtttgagac cagcctggcc accatggtga aaccccatct ctactaaaaa tacaaaaatt   13260
agccgggctt ggtggtgagc acctgtaatc ccaccctgcc gagtggcagg ctgaggcagg   13320
agaatcgctt gagcccaaga gccggaggtt gcagtgagcc aagcttgcac cattgcactc   13380
cagcctaggc aacagagtgt gactccatct caagaaaaaa aaaattctat ttcattttac   13440
aatatgcaga tatatgtcca tacacatgca taatataaat gtataccata tttgtgagaa   13500
tatgcatata tgtacacatt agatacacaa tacaagcaca atacatatgt cttttgccca   13560
agatacagca ttttgtaaag gagacaggaa tttagtaata tatgttccag aaacagtaca   13620
caagagaatt cgccgagatg agaaagttgt cactaggaat ggggagtggt aagatgtaga   13680
aggtataatt gttcttaaag ttctactgcc aactctttcc aattaattac ccactctgcc   13740
atgctttatg gacaggaggt tgtcggacac tgtcaattaa taaatatttg agcatgatac   13800
actgcttgga gctcctctaa tataggagag tgatatccta gtgcatgtta cagagggagt   13860
gtccacacag ttcctattgt catttgatga gttacttttc aggggccttg tacctgagca   13920
agttgtcctc tttttgatgg atttcagatt gagttacctg cattgtcttg agattgcagc   13980
gtgtttcctc cactgtacgg cgtagtcagc agatctatta gttaaactcc agtgggccct   14040
cagtcactaa atctatcctc tgtgttgaag gctttctgca tttgcctttc aataaaggtt   14100
tagaataact cctt                                                   14114
```